US007317945B2

(12) United States Patent
Litvak et al.

(10) Patent No.: US 7,317,945 B2
(45) Date of Patent: Jan. 8, 2008

(54) METHOD AND SYSTEM TO CONVEY THE WITHIN-CHANNEL FINE STRUCTURE WITH A COCHLEAR IMPLANT

(75) Inventors: Leonid M. Litvak, Los Angeles, CA (US); David A. Krubsack, Saugus, CA (US); Edward H. Overstreet, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 914 days.

(21) Appl. No.: 10/712,078

(22) Filed: Nov. 13, 2003

(65) Prior Publication Data
US 2004/0136556 A1 Jul. 15, 2004

Related U.S. Application Data

(60) Provisional application No. 60/426,267, filed on Nov. 13, 2002.

(51) Int. Cl.
*A61N 1/00* (2006.01)
(52) U.S. Cl. .......................................... 607/57; 704/214
(58) Field of Classification Search .................. 607/55, 607/56, 57, 137; 704/214
See application file for complete search history.

(56) References Cited

U.S. PATENT DOCUMENTS

| 3,751,605 | A | 8/1973 | Michelson |
| 4,400,590 | A | 8/1983 | Michelson |
| 4,495,384 | A | 1/1985 | Scott et al. |
| 4,819,647 | A | 4/1989 | Byers et al. |

(Continued)

FOREIGN PATENT DOCUMENTS

WO    WO-00/01200 A1    1/2000

(Continued)

OTHER PUBLICATIONS

Harnsberger, et al., "Perceptual vowel "spaces" of Cochlear Implant User: Implications for the Study of Auditory Adaptation to Spectral Shift", J Acoust Soc Am, vol. 109(5) pt. 1, (May 2001), pp. 2135-2145.

(Continued)

*Primary Examiner*—Ehud Gartenberg
*Assistant Examiner*—Jonathan B Thomas
(74) *Attorney, Agent, or Firm*—Philip H. Lee; Bryant R. Gold; Victoria A. Poissant (57) ABSTRACT

The present invention provides a cochlear stimulation system and method for capturing and translating fine time structure ("FTS") in incoming sounds and delivering this information spatially to the cochlea. The system comprises a FTS estimator/analyzer and a current navigator. An embodiment of the method comprises analyzing the incoming sounds within a time frequency band, extracting the slowly varying frequency components and estimating the FTS to obtain a more precise dominant FTS component within a frequency band. After adding the fine structure to the carrier to identify a precise dominant FTS component in each analysis frequency band (or stimulation channel), a stimulation current may be "steered" or directed, using the concept of virtual electrodes, to the precise spatial location (place) on the cochlea that corresponds to the dominant FTS component. This process is simultaneously repeated for each stimulation channel and each FTS component.

22 Claims, 8 Drawing Sheets

U.S. PATENT DOCUMENTS

| | | | |
|---|---|---|---|
| 5,603,726 | A | 2/1997 | Schulman et al. |
| 5,626,629 | A | 5/1997 | Faltys et al. |
| 5,938,691 | A | 8/1999 | Schulman et al. |
| 6,052,624 | A | 4/2000 | Mann |
| 6,067,474 | A | 5/2000 | Schulman et al. |
| 6,078,838 | A | 6/2000 | Rubinstein |
| 6,129,753 | A | 10/2000 | Kuzma |
| 6,157,861 | A | 12/2000 | Faltys et al. |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,219,580 | B1 | 4/2001 | Faltys et al. |
| 6,249,704 | B1 | 6/2001 | Maltan et al. |
| 6,289,247 | B1 | 9/2001 | Faltys et al. |
| 6,295,467 | B1 | 9/2001 | Kollmeier et al. |
| 6,393,325 | B1 | 5/2002 | Mann et al. |
| 6,415,185 | B1 | 7/2002 | Maltan |
| 6,565,503 | B2 * | 5/2003 | Leysieffer et al. ............ 600/25 |
| 6,980,864 | B2 * | 12/2005 | Faltys et al. ................ 607/116 |
| 7,149,583 | B1 * | 12/2006 | Litvak ......................... 607/57 |
| 2003/0167077 | A1 * | 9/2003 | Blamey et al. ............... 607/57 |

FOREIGN PATENT DOCUMENTS

| | | |
|---|---|---|
| WO | WO 02/09808 A1 | 2/2002 |
| WO | WO-03/015863 A2 | 2/2003 |

OTHER PUBLICATIONS

McDermott, et al., "Pitch Ranking with Nonsimultaneous Dual-Electrode Electrical Stimulation of the Cochlea", J Acoust Soc Am, vol. 96(1), (1994) pp. 155-162.

Morse, et al., "The practical Use of Noise to Improve Speech Coding by Analogue Cochlear Implants", Chaos, Solutions and Fractals, vol. 11, No. 12, (2000) pp. 1885-1894.

Rubinstein et al., "The Neurophysiological Effects of Simulated Auditory Prosthesis Simulation" Second Quarterly Progress Report NO1-DC-6-2111.

Scheirer, et al., "Construction and Evaluation of Robust Multifeature Speech/Music Discriminator", Acoustics, Speech, and Signal Processing (1997), IEEE International Conference on Munich, Germany (Apr. 21-24, 1997), pp. 1331-1334.

Smith, et al., "Chimaeric Sounds, Reveal Dichotomies in Auditory Perception", Nature, vol. 416, No. 6876, (Mar. 7, 2002), pp. 87-90.

van Wieringen, et al., "Comparison of Procedures to Determine Electrical Stimulation Thresholds in Cochlear Implant Users", Ear and Hearing, vol. 22(6), (2001), pp. 528-538.

Zeng, et al., ":Loudness of Simple and Complex Stimuli in Electric Hearing", Annals of Otology, Rhinology & Laryngology, vol. 104 (9), (1995) pp. 235-238.

Zhang, et al., "Loudness of Dynamic Stimuli in Acoustic and Electric Hearing", J Acoust Soc Am, vol. 102(5) Pt. 1, (Nov. 1997), pp. 2925-2934.

Overstreet, Litvak, and Faltys inventors for AB-378U; U.S. Appl. No. 10/698,097, filed Oct. 31, 2003, entitled "Multi-Electrode Stimulation to Elicit Electrically-Evoked Compound Action Pontial."

Litvak, inventor for AB-396U; U.S. Appl. No. 10/819,609, filed Apr. 7, 2004, entitled "Method of Using Non-Simultaneous Stimulation to Represent the Within-Channel Fine Structure."

* cited by examiner

METHOD AND SYSTEM TO CONVEY THE WITHIN-CHANNEL FINE STRUCTURE WITH A COCHLEAR IMPLANT

The present application claims the benefit of U.S. Provisional Patent Application Ser. No. 60/426,267, filed 13 Nov. 2002, which application is herein incorporated by reference in its entirety.

BACKGROUND OF THE INVENTION

The present invention relates to systems and methods for stimulating the cochlea. More specifically, the present invention relates to systems and methods for processing incoming sound wave information and accurately conveying this information as perceived sounds.

Fine time structure ("FTS") is the fast varying information present in sounds. The FTS has been shown to be essential for recognition of musical melodies, as well as for finely discerning other sounds.

In conventional, pulsatile, cochlear, implantable stimulation strategy ("CIS"), the incoming sound is broken into a small number of frequency bands, for example, between 8 to 22 bands. The slowly-varying envelope is extracted from each band and this envelope information is used to modulate a high-frequency pulsatile carrier signal that is presented to a plurality of stimulating electrodes, conventionally equaling the number of frequency bands. In this conventional method of processing sound, some of the FTS information is discarded, namely, the fast-varying components present in each frequency band (or stimulation channel).

FTS can be conveyed to the auditory nerve fibers in two different ways: (a) temporally, with respect to the discharge patterns of the auditory nerve fibers over time; and (b) spectrally (spatially), with respect to the cochlear excitation pattern over the length of the cochlea. Because different segments of the cochlea, over its length, are associated with different sound frequencies, the spatial location on the cochlea represents the spectral frequencies of the incoming sounds. It is unclear which of the two modes of variation, temporal or spectral, is more important for conveying the FTS.

In a conventional CIS system, the use of discrete electrodes fixes the position of the electrical stimulation field emanating from each electrode. Thus, if eight electrodes are used, there are eight dominant, but fixed, stimulation points on the cochlea. Spatial points or places on the length of the cochlea, which are between electrodes and between the dominant stimulation points, are poorly stimulated because only those areas closest to the electrodes are well stimulated. As a result, the conventional system can not accurately convey the FTS spatially to the cochlea.

It would be desirable to capture the FTS in incoming sounds and to deliver this information with improved spatial accuracy over the length of the cochlea. What is needed, therefore, is a method and system of processing auditory sound waves into electrical signals that capture FTS information and accurately direct this information to appropriate nerves that spatially innervate the cochlea.

SUMMARY OF THE INVENTION

The present invention addresses the above and other needs by providing a stimulation strategy that accurately conveys the FTS.

In one aspect of the present invention, there is provided a method for capturing the FTS in filter outputs, processing this information and delivering a more accurate spectral translation of the sound to the cochlea. In accordance with the present invention for stimulating the cochlea, the method comprises: (a) analyzing the incoming sounds within a plurality of frequency bands; (b) extracting the slowly varying frequency carrier component of the incoming sound in each frequency band with an envelope; (c) estimating the dominant FTS component in each frequency band using an FTS analyzer; (d) adding the dominant FTS component to the carrier component to provide a precise corresponding spatial location on the cochlea; and (e) directing the stimulation current, using a current navigator, to the precise spatial place on the cochlea.

It is a feature of the present invention to provide embodiments of a method for analyzing the FTS which involve: (1) within a predetermined time interval, for a particular frequency band or window, averaging the intervals between the zero crossings of an incoming sound wave and calculating the dominant FTS component or (2) in a predetermined time interval, using a Fast Fourier Transform to de-construct a sound wave, in order to identify the dominant FTS component in each particular frequency band or window.

In another aspect of the invention a stimulation system is provided, which system comprises: an envelope extractor for extracting the slowly varying information in a sound; an FTS analyzer for identifying and estimating the dominant FTS component within a frequency band; and a current navigator for directing stimulation, using virtual electrodes, to more accurately stimulate specific sets of nerves along the cochlea.

It is a feature of the present invention that capturing FTS and conveying this information to corresponding locations or "places" along the cochlea can be implemented in conjunction with such concepts as M of N stimulation strategies, as well as virtual channels/electrodes.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Before describing the present invention, it will be helpful to first provide an overview of the structure of a cochlear implant system that can be used to practice the present invention. This overview is provided below in connection with the description of FIGS. 1, 2A and 2B.

Figure 1:
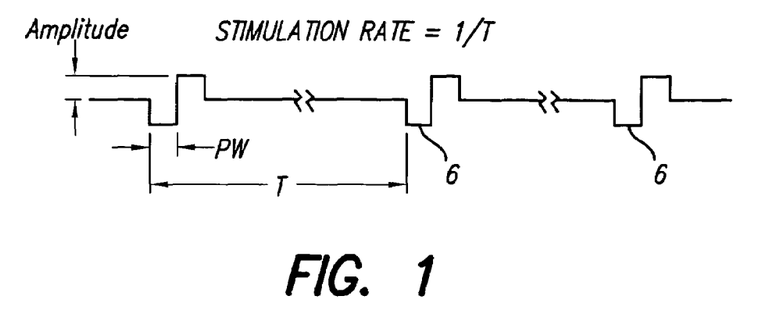
FIG. 1 is a current stimulation waveform that defines the stimulation rate (1/T) and biphasic pulse width (PW) associated with electrical stimuli, as those terms are commonly used in the neurostimulation art.

FIG. 1, shows a waveform diagram of a biphasic pulse train. The figure defines stimulation rate (1/T), pulse width (PW) and pulse amplitude as those terms are commonly used in connection with a neurostimulator device, such as a cochlear implant, a spinal cord stimulator (SCS), a deep brain stimulator (DBS), or other neural stimulator. All such systems commonly generate biphasic pulses 6 of the type shown in FIG. 1 in order to deliver stimulation to tissue.

A "biphasic" pulse 6 consists of two pulses: a first pulse of one polarity having a specified magnitude, followed immediately or after a very short delay by a second pulse of the opposite polarity, although possibly of different duration and amplitude, such that the total charge of the first pulse equals the total charge of the second pulse. It is thought that such charge-balancing can prevent damage to stimulated tissue and prevent electrode corrosion. For multichannel cochlear stimulators of the type that may include the present invention, it is common to apply a high rate biphasic stimulation pulse train to each of the pairs of electrodes in accordance with a selected strategy and modulate the pulse amplitude of the pulse train as a function of information contained within the sensed acoustic signal.

Figure 2A:
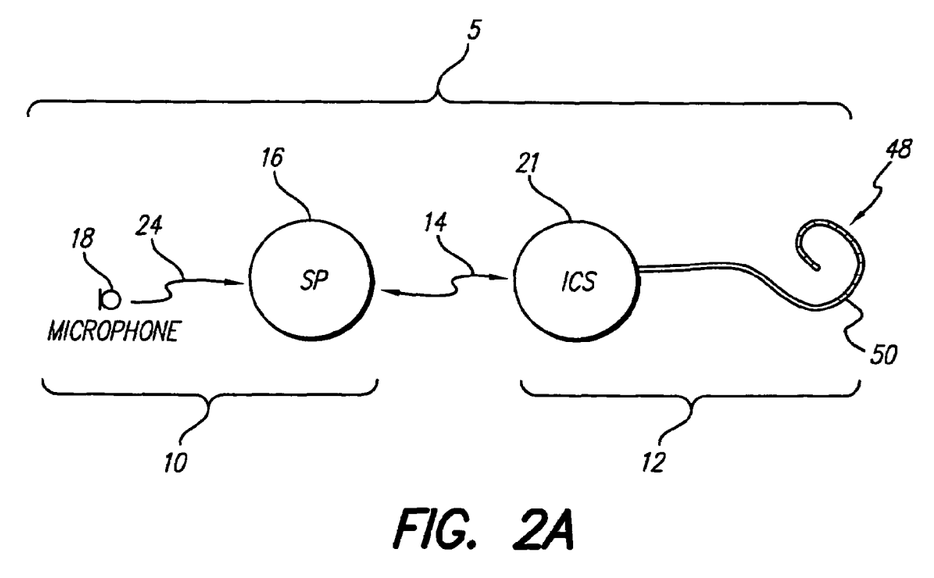
FIGS. 2A and 2B, respectively, show a cochlear implant system and a partial functional block diagram of one embodiment of a cochlear stimulation system, which may incorporate the system of the present invention and implement the method of the present invention for conveying fine time structure in sounds.

FIG. 2A shows a cochlear stimulation system 5 that includes a speech processor portion 10 and a cochlear stimulation portion 12. The speech processor portion 10 includes a speech processor (SP) 16 and a microphone 18. The microphone 18 may be connected directly to the SP 16 or coupled to the SP 16 through an appropriate communication link 24. The cochlear stimulation portion 12 includes an implantable cochlear stimulator (ICS) 21 and an electrode array 48. The electrode array 48 is adapted to be inserted within the cochlea of a patient. The array 48 includes a plurality of electrodes 50, e.g., sixteen electrodes, spaced along the array length and which electrodes are selectively connected to the ICS 21. The electrode array 48 may be substantially as shown and described in U.S. Pat. Nos. 4,819,647 or 6,129,753, both patents incorporated herein by reference. Electronic circuitry within the ICS 21 allows a specified stimulation current to be applied to selected pairs or groups of the individual electrodes included within the electrode array 48 in accordance with a specified stimulation pattern defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system and the ICS 21 and electrode array 48 comprise the implantable portion of the system. Thus, the data link 14 is a transcutaneous (through the skin) data link that allows power and control signals to be sent from the SP 16 to the ICS 21. In some embodiments, data and status signals may also be sent from the ICS 21 to the SP 16.

Figure 2B:
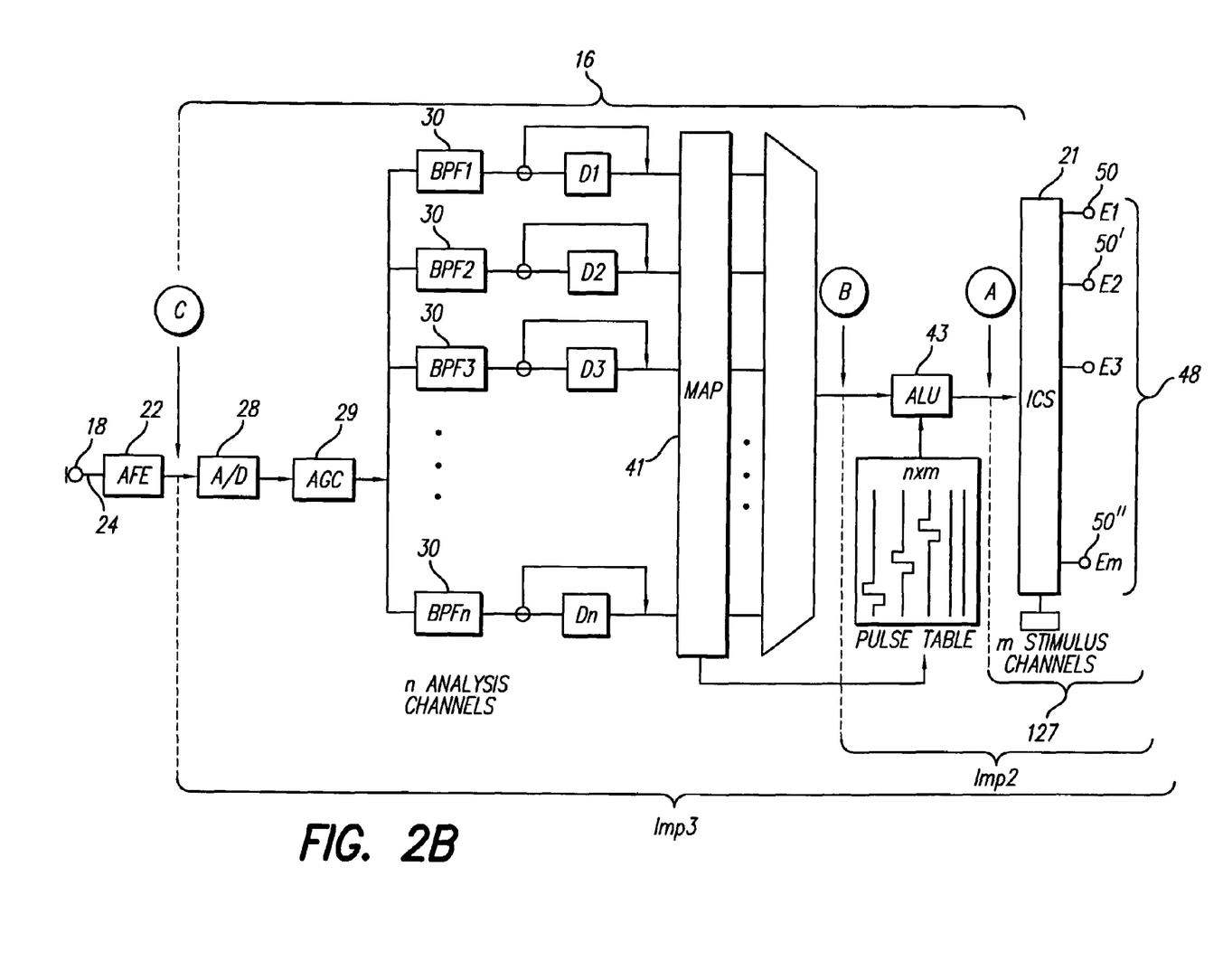

FIG. 2B shows a partial block diagram of one embodiment of a cochlear implant system that can include the present system and that can permit the practice in accordance with the present method for conveying FTS. At least certain portions of the SP 16 can be included within the implantable portion of the overall cochlear implant system, while other portions of the SP 16 can remain in the external portion of the system. In general, at least the microphone 18 and associated analog front end (AFE) circuitry 22 can be part of the external portion of the system and at least the ICS 21 and electrode array 48 can be part of the implantable portion of the invention. As used herein, the term "external" means not implanted under the skin or residing within the inner ear. However, the term "external" can also mean residing within the outer ear, residing within the ear canal or being located within the middle ear.

Typically, where a transcutaneous data link must be established between the external portion and implantable portions of the system, such link is implemented by using an internal antenna coil within the implantable portion, and an external antenna coil within the external portion. In operation, the external antenna coil is aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be implemented with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses sound waves and converts such sound waves to corresponding electrical signals and thus functions as an acoustic transducer. The electrical signals are sent to the SP 16 over a suitable electrical or other link 24. The SP 16 processes these converted acoustic signals in accordance with a selected speech processing strategy to generate appropriate control signals for controlling the ICS 21. Such control signals specify or define the polarity, magnitude, location (which electrode pair or electrode group receive the stimulation current), and timing (when the stimulation current is applied to the electrode pair) of the stimulation current that is generated by the ICS. Such control signals thus combine to produce a desired spatio-temporal pattern of electrical stimuli in accordance with a desired speech processing strategy.

A speech processing strategy is used, among other reasons, to condition the magnitude and polarity of the stimulation current applied to the implanted electrodes of the electrode array 48. Such speech processing strategy involves defining a pattern of stimulation waveforms that are to be applied to the electrodes as controlled electrical currents.

FIG. 2B depicts the functions that are carried out by the SP 16 and the ICS 21. A description of the functional block diagram of the cochlear implant shown in FIG. 2B is found in U.S. Pat. No. 6,219,580, incorporated herein by reference.

It is emphasized that the particular functions shown in FIG. 2B are representative of just one type of signal processing strategy that may be employed for dividing the incoming signal into frequency bands and independently processing each band. The system and method of the present invention for conveying FTS information may be used with other cochlear systems other than the system shown in FIG. 2B, which system is not intended to be limiting to the present invention.

The cochlear implant functionally shown in FIG. 2B provides n analysis channels that may be mapped to one or more stimulus channels. That is, as seen in FIG. 2B, after the incoming sound signal is received through the microphone 18 and the analog front end circuitry (AFE) 22, the signal can be digitized in an analog to digital (A/D) converter 28 and then subjected to appropriate gain control (which may include compression) in an automatic gain control (AGC) unit 29. After appropriate gain control, the signal can be divided into n analysis channels 30, each of which includes a bandpass filter, BPFn, centered at a selected frequency. The signal present in each analysis channel 30 is processed as described more fully in the U.S. Pat. No. 6,219,580 patent, or as is appropriate, using other signal processing techniques and the signals from each analysis channel may then be mapped, using mapping function 41, so that an appropriate stimulus current of a desired amplitude and timing may be applied through a selected stimulus channel to stimulate the auditory nerve.

Thus it is seen that the exemplary system of FIG. 2B provides a plurality of analysis channels, n, wherein the incoming signal is analyzed. The information contained in these n analysis channels is then appropriately processed, compressed and mapped in order to control the actual stimulus patterns that are applied to the user by the ICS 21 and its associated electrode array 48.

The electrode array 48 includes a plurality of electrode contacts 50, 50, 50" and labeled as, E1, E2, . . . Em, respectively, which are connected through appropriate conductors to respective current generators or pulse generators within the ICS. Through these plurality of electrode contacts, a plurality of stimulus channels 127, e.g., m stimulus channels, may exist through which individual electrical stimuli can be applied at m different stimulation sites within the patient's cochlea.

Conventional cochlear implant systems use a one-to-one mapping scheme between the n analysis channels and the m stimulus channels 127 that are directly linked to m electrodes 50, 50', 50", such that n analysis channels=m electrodes. In such a case, the signal resulting from analysis in the first analysis channel may be mapped, using appropriate mapping circuitry 41 or equivalent, to the first stimulation channel via a first map link, resulting in a first cochlear stimulation place (or first electrode). Similarly, the signal resulting from analysis in the second analysis channel of the SP may be mapped to a second stimulation channel via a second map link, resulting in a second cochlear stimulation place, and so on. Obviously, there is little point to having more analysis channels than the number of stimulation channels/electrodes that are available.

In contrast, the present invention may be used under the condition that n=m or when n is greater than m. For example assume that n is at least 20 or as high as 32, while m is no greater than sixteen, e.g., 8 to 16. In that case, it may be possible to use n analysis channels even though there are actually fewer physical electrodes than analysis channels. This may be done using the concept of "virtual electrodes."

Virtual electrodes provide stimulation 6 at parts of the cochlea that are "in between" electrodes. An equivalent stimulus is perceived which would be produced if a "virtual electrode" were located on that location or "place" on the cochlea. Advantageously, the capability of using different mapping schemes between n SP analysis channels and m ICS stimulation channels 127 to thereby enable a large number of "in-between", as well as actual stimulation sites can more accurately direct the neural excitation to the cochlear location or "place" which is targeted.

One method of implementing virtual electrodes is to use two or more stimulus output channels 127 to deliver stimuli simultaneously at two or more electrode contacts 50, 50', 50". The stimulus current 6 at each electrode is weighted in appropriate proportions between two or more electrodes 50, 50' 50" in order to effectively "steer" the current from one stimulus location within the cochlea to another. The concept of "current steering" is taught in U.S. Pat. No. 6,393,325 for use within a spinal cord stimulation system and U.S. Pat. No. 6,052,624. Both patents are incorporated herein by reference. Current steering, as taught in the U.S. Pat. No. 6,393,325, may be employed within other neural stimulation systems, including a cochlear implant system. Additional features and advantages of current steering are taught in International Publication Number WO 02/09808 A1, published Feb. 7, 2002, based on International Application Number PCT/US00/20294, filed 26 Jul. 2000, which publication is incorporated herein by reference in its entirety.

It is important to understand that the concept of "virtual electrodes" is a broad concept and includes the above described method of current steering using weighted currents simultaneously delivered through two or more electrodes. Virtual electrodes can also be created by other techniques. One such alternative technique is to provide rapidly alternating, non-simultaneous, stimuli at a first electrode $E_f$ and at a second electrode $E_s$, wherein the effect of this time-multiplexed, alternating stimulus delivery is to provide a perceived stimulation that is somewhere between $E_f$ and $E_s$. The present invention may utilize all techniques of implementing virtual electrodes, including current steering through application of simultaneous weighted currents and also through time-multiplexed presentation of stimuli delivered through at least two different closely positioned electrodes 50, 50', 50".

Figure 3:
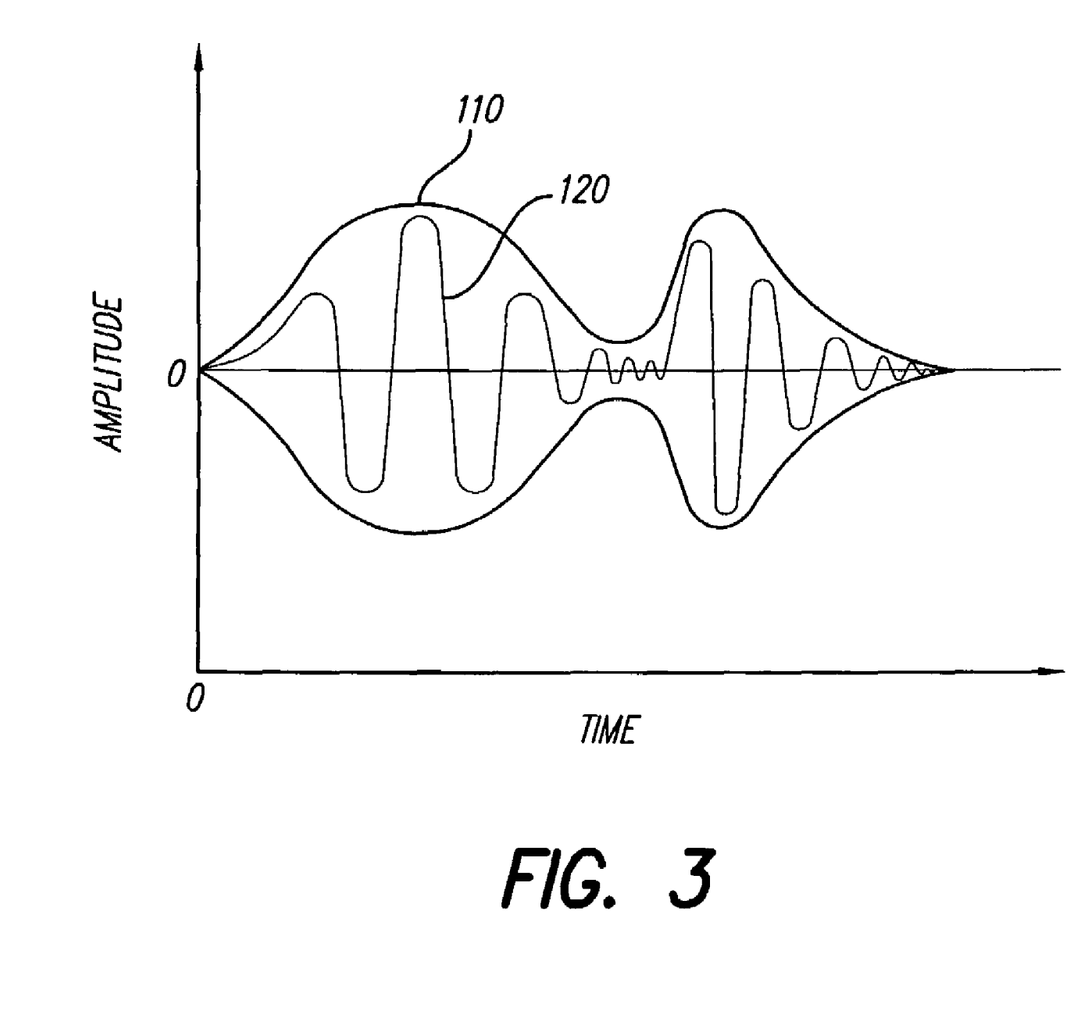
FIG. 3 shows a representation of sound wave amplitudes as a function of time and a slowly moving envelope.
Figure 4A:
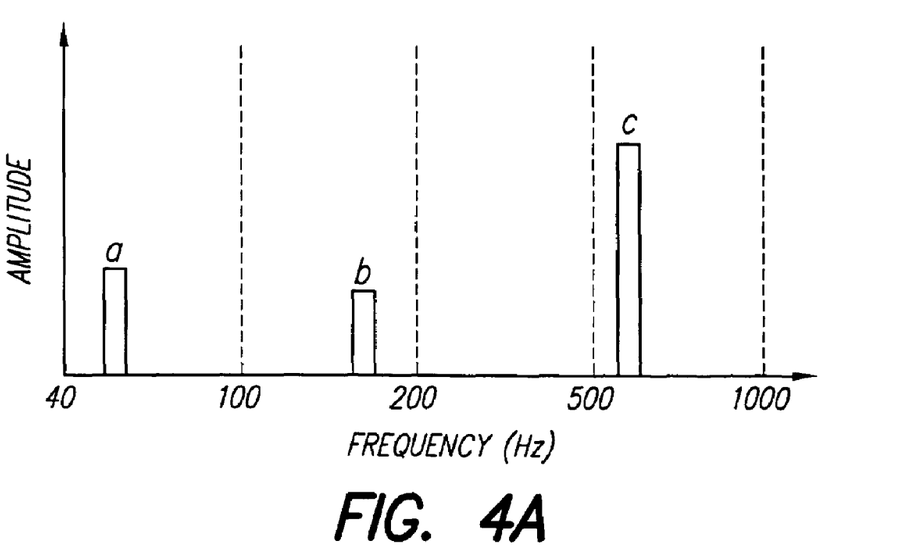
FIG. 4A shows a graph depicting four frequency bands or windows with dominant FTS components a, b and c.
Figure 4B:
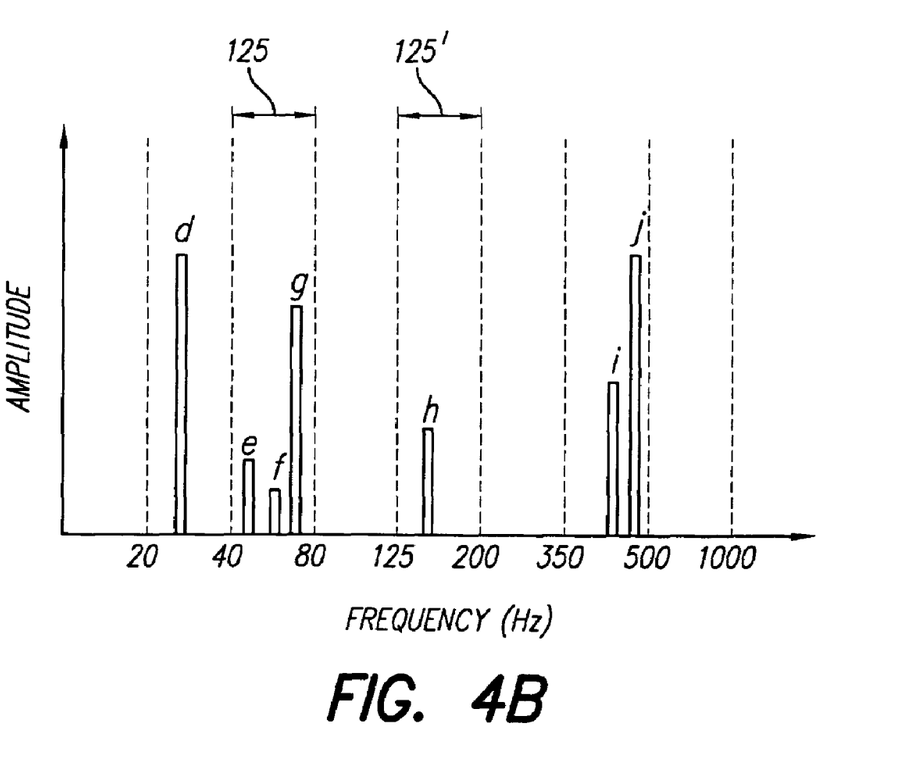
FIG. 4B shows a graph depicting eight frequency bands or windows with dominant FTS components d, g, h, and j.

FIG. 3 shows a representation of incoming sound waves as a function of time that could be picked up by microphone 18 as shown in FIG. 2B. The envelope 110 of the sound provides the slow moving or lower frequency components of the sound. The faster varying components 120, within this envelope 110 of the incoming sound are FTS components of the sound. Conventional cochlear stimulation systems take the incoming sounds, as represented in FIG. 3 and deconstruct the sounds into frequency bands, as shown in FIGS. 4A and 4B. These frequency bands may correspond to bandpass filters $BPF_1, \ldots BPF_N$ shown in FIG. 2B.

FIG. 4A provides a specific example in which incoming sounds are processed into four separate frequency bands, shown as 40-100 Hz, 100-200 Hz, 200 to 500 Hz and 500 to 1000 Hz in this particular example. The four frequency bands may represent four distinct stimulation channels, in the instance where n analysis channels=m stimulation channels. To implement the four channel processing (without the use of virtual electrodes), at least four stimulating electrodes are required to convey the necessary stimuli to the cochlea. The dominant fine time structure (FTS) components a, b and c occur in three of four frequency bands shown. Minor peaks may be present but are not illustrated here, as they are ignored in processing. The third frequency band does not show any activity.

To convey the identified, dominant FTS in each band, the stimulation system delivers stimulation pulses to three of four electrodes that are placed on the cochlea. The specific amplitudes of each dominant FTS component that is translated to stimulus pulses through the appropriate three of the electrodes can be translated as a perceived sound intensity. This perceived sound intensity can be increased by increasing the stimulation amplitude of a pulse such that more nerve fibers are recruited (captured) at one time. In addition, the frequency of the train of pulses delivered at the electrode can also be increased to recruit more nerve fibers within a fixed time interval. Such an increase in pulse frequency and amplitude can translate to an increase in perceived, sound intensity.

FIG. 4B provides another specific example of an eight-channel system in which the sound frequency spectrum, from 0 Hz to 1 kHz, is divided into eight frequency bands 125, 125'. Dominant FTS components within each frequency analysis band 125, 125' shown are d, g, h, and j. These dominant FTS components are identified, selected and captured by the cochlear stimulation system. Minor peaks e, f and i are discarded or are not identified. In such an eight-channel system (where n analysis channels=m stimulation channels), there should be at least eight electrodes in the electrode array, each electrode 50, 50', 50" representing one analysis channel 30. As illustrated in FIG. 4B, when the sound spectrum is broken into more frequency bands to capture more FTS, the resolution of the stimulation system is enhanced because it will be able to capture smaller components such as e and f. Thus, it can be appreciated that higher resolution can be obtained by having more analysis channels ($BPF_1$ ... $BPF_N$), for example, using sixteen different channels employing a sixteen electrode array 48. On the other hand, there is a practical limit to increasing the number of frequency analysis bands that can be used in a cochlear stimulator because of space and power limitations of the device.

It is important to understand however, that even in a system having many analysis channels, e.g., sixteen, there is a loss of FTS information because, while the dominant FTS component, for instance, g, shown in FIG. 4B, is identified within a single frequency band (40-80 Hz), the conventional stimulation system does not further attempt to convey the exact frequency of the FTS component within that band. Rather, it is conveyed generally by the fixed position of an electrode that represents that particular frequency band. It is assumed that the dominant frequency is centered and fixed somewhere in the middle of an analysis frequency band (or band-pass frequency). This limitation is inherent in any conventional cochlear stimulation systems because each electrode is placed in a fixed location with respect to the electrode array and, when the array is implanted, each electrode is fixed with respect to the cochlea. As a result, FTS frequency information is lost.

Figure 5A:
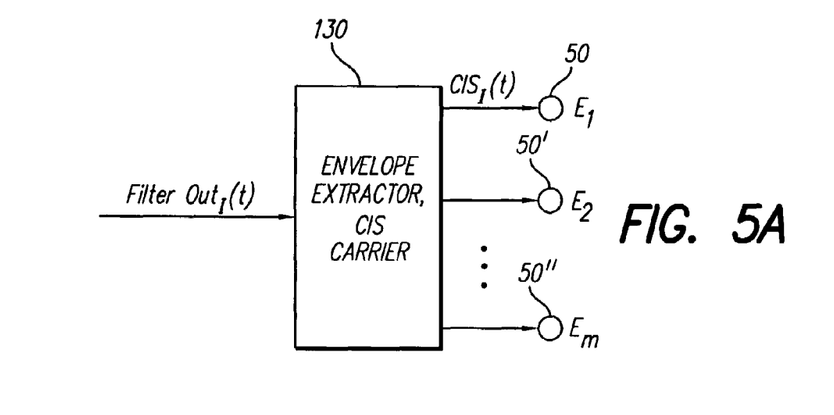
FIG. 5A shows a block functional diagram representing conventional sound processing in a cochlear implant using an envelope extractor.

FIG. 5A shows a partial block diagram of the processing system and method that are presently practiced in conventional cochlear stimulation systems and can be used to illustrate how FTS is lost. The concept of virtual electrodes is not employed in a conventional system. After filtering out the dominant frequency components in each frequency band using an envelope extractor, as shown by the rectangular box 130, the dominant frequency component is conveyed to the respective electrode 50, 50', 50" that corresponds to that particular frequency band. It can be seen that the position of a dominant frequency, for example, component c in FIG. 5A will be positioned on the cochlea, spectrally in the middle of the frequency band between 500 Hz to 1000 Hz, instead of closer to the 500 Hz as shown.

Figure 5B:
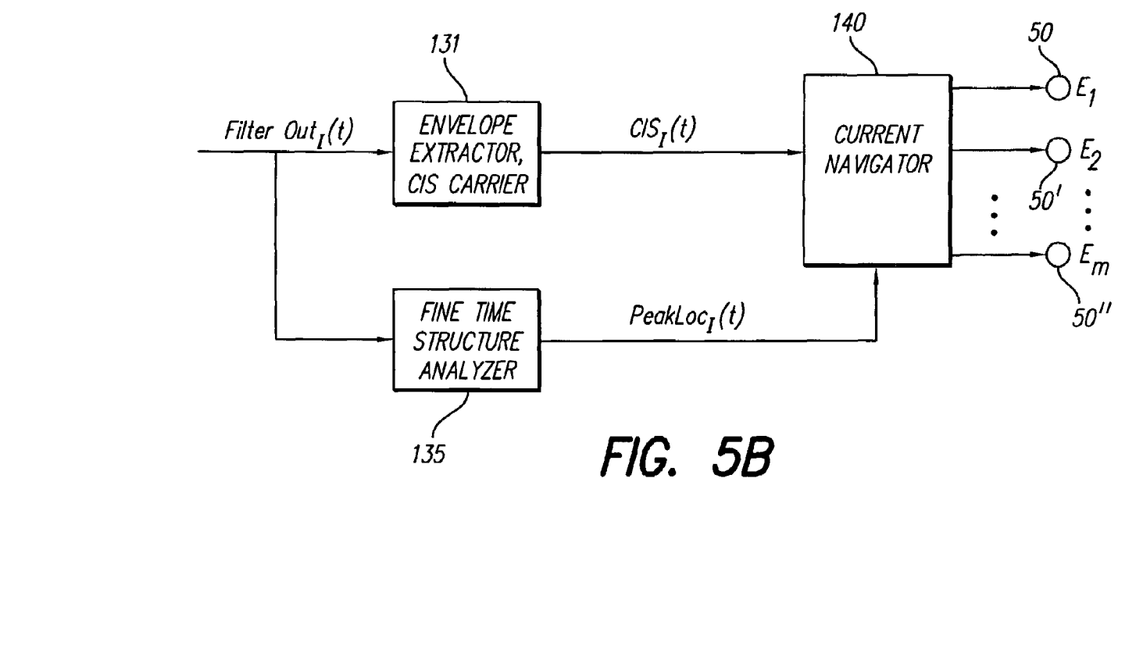
FIG. 5B shows a block functional diagram representing the system and method of the present invention, which includes an FTS analyzer/estimator and a current navigator.

The block diagrams of FIGS. 5A and 5B show that both the conventional cochlear stimulator system and the system of the present invention includes an envelope extractor 130 and 131 for providing the carrier signal, and a linear array of m electrodes, $E_1, E_2 \ldots E_m$, which are represented as 50, 50', and 50", respectively.

FIG. 5B shows, in accordance with the present invention, a block diagram of a cochlear stimulation system which captures the FTS information in the auditory stimulation signals and conveys this information spatially (spectrally) to the nerves in the cochlea. The system shown in FIG. 5B includes: (a) an envelope extractor 131; (b) a fine time structure (FTS) analyzer/estimator 135; and (c) a current navigator 140 for creating virtual electrodes in order to precisely direct stimuli to various spatial locations (the place) on the cochlea that correspond to the FTS captured and analyzed by the FTS analyzer 135. The task of the FTS analyzer 135 is to precisely estimate the dominant FTS components in each frequency band as, for example, shown previously in FIG. 5B. Assuming a stimulation system which has eight analysis frequency bands, the FTS analyzer 135 determines the dominant FTS component within each analysis frequency band. The dominant FTS component within each band is identified, including the dominant component's precise frequency within the band. The other minor FTS components within a frequency band (such as inferior components e and f, in FIG. 5B) can be discarded.

The obtained FTS is then linearly added to the carrier signal obtained from the envelope extractor 131 by the current navigator 140 which processes and spatially directs the presentation of stimuli on the various cochlear places via one or more electrodes 50, 50', 50" such that the peak of the stimulation will be presented more precisely at the cochlear locations (places) that correspond to the FTS dominant frequency components in each frequency band.

Figure 6:
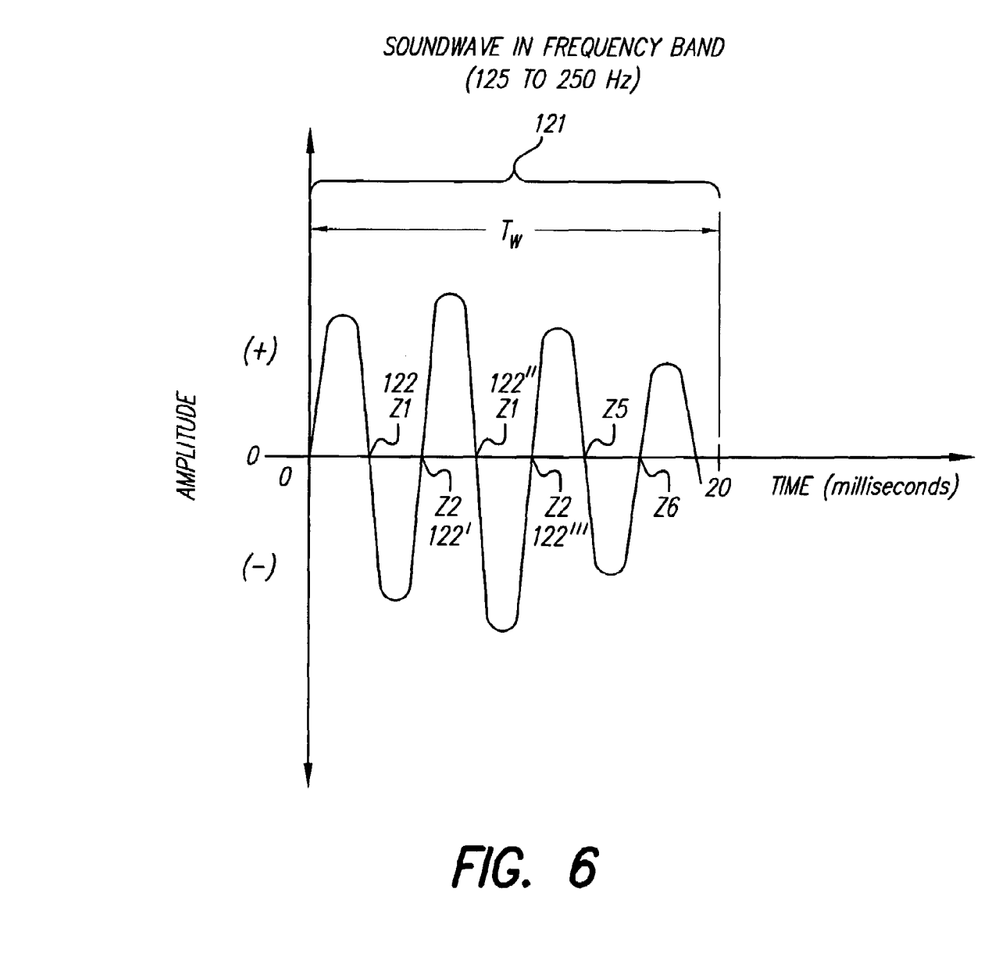
FIG. 6 shows, in accordance with the present invention, a depiction of a filter output which is one frequency band, wherein the dominant FTS frequency component is calculated by averaging the intervals between zero crossings of the waveform or counting the number of zero crossings of a waveform and averaging the result.

FIG. 6 shows a graph, in accordance with the present invention, one method for determining the dominant FTS component (the precise frequency) within a frequency band. The graph shows a sampled time window, $T_w$, 121 of 20 milliseconds sampling sounds within a single frequency band of 125 to 250 Hz. The dominant FTS component within this frequency band can be calculated by averaging the time intervals between successive zero crossings, 122, 122', 122" also labeled in FIG. 6 as Z1, Z2, Z3, Z4, Z5 and Z6 within a time window, $T_w$, illustrated here as 20 milliseconds. The peak FTS estimate is simply 1 over the averaged intervals of time between successive zero crossings. For example, the intervals of time are represented by the time between Z2 and Z1; the time between Z3 and Z2, the time between Z4 and Z3, the time between Z5 and Z4 and the time between Z6 and Z5. Although the example shows a time window, $T_w$, of 20 milliseconds, a time window of between about 10 to 100 milliseconds may be used to smooth the estimate so that stimulation is not perceived as noisy.

Another, alternative embodiment of the present method for determining the FTS of the dominant component is to count zero crossings of the sound waves in a predetermined time window. The number of zero crossings is divided by the total duration of the time window to achieve the frequency estimate. For instance, both positive and negative going crossings are counted (in this case seven), then the number of zero crossings is further divided by 2 and then divided again by the total duration of time, $T_w$, 121, which is 20 milliseconds. Sufficiently accurate estimates can be achieved with a time window, $T_w$, that is at least 10 milliseconds long and preferably between about 10 to 100 milliseconds.

Still another alternative method of the present invention for determining the dominant FTS component is somewhat more sophisticated and employs a Fast Fourier Transform to precisely de-construct the fundamental frequency components in a particular incoming sound. The dominant FTS component in a frequency band should be sustained over a time duration of about between 10 to 100 milliseconds. A formant tracker, which can identify the dominant FTS components in a frequency band can be employed. A hardware and software implementation that uses a Fast Fourier Transform may, however, may require greater processing power and, therefore, use more energy and use up more device space compared to the simple method described which needs only detection and counting of zero crossings.

Once the specific dominant FTS in each of the frequency bands are identified by one of the methods identified above, the dominant FTS must be conveyed spatially (spectrally) to the specific locations of the cochlea. Conventional stimulation systems do not convey via the electrodes the precise dominant FTS components because the electrodes in the electrode array are fixed at specific locations on the array and in the cochlea, after the array is implanted.

Figure 7A:
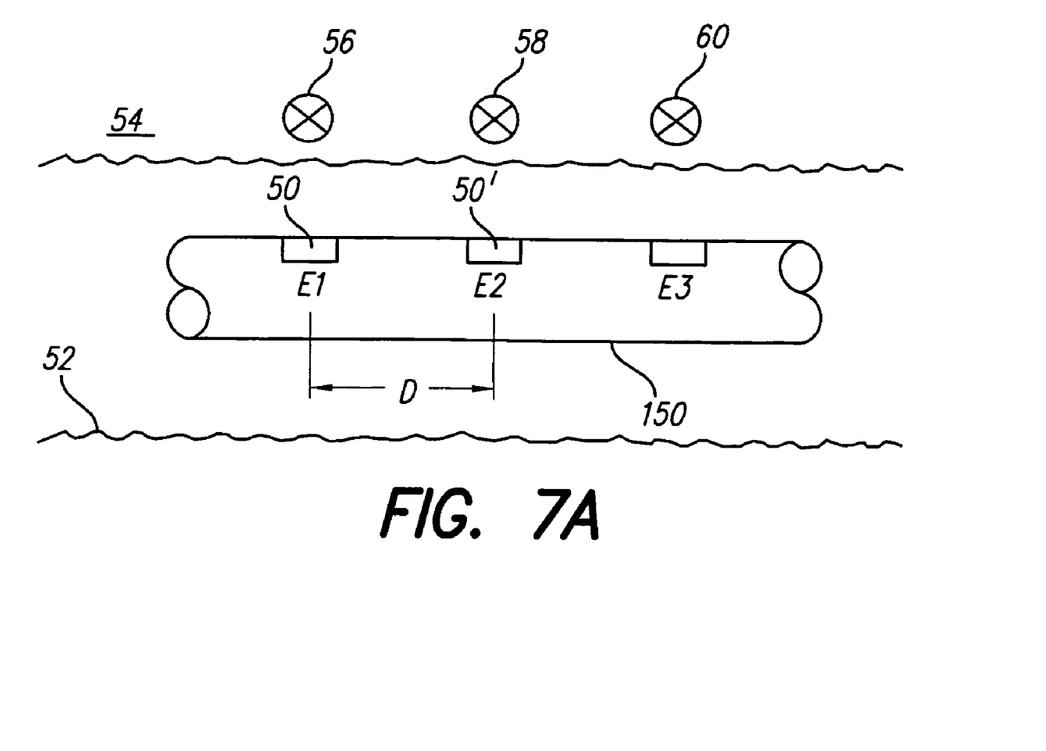
FIG. 7A illustrates the location of an applied stimulus within a duct of the cochlea, without the benefit of virtual electrodes.

FIG. 7A shows a side view of part of an electrode array showing electrodes, E1, 50, E2, 50', and E3, with inter-electrode spacing, D. This illustrates conventional stimulation, without employing virtual electrodes. The carrier 150 that has the electrodes E1, E2 and E3 is shown inserted into a cochlear duct 52, e.g., the scala tympani, within tissue 54 that is to be stimulated. The electrodes E1, E2 and E3 are located "in line" on a carrier 150, and are spaced apart from each other a distance "D". Each electrode is electrically connected to a wire conductor (not shown) that is embedded within the carrier 150, and which connects the electrode to the ICS 21 (see FIGS. 2A or 2B). The cochlear duct 52, is typically one of the three ducts in the human cochlea, for instance, the scala tympani. A reference (indifferent) electrode (not shown) is also presumed to be present some distance from the electrodes E1, E2 and E3, thereby allowing monopolar stimulation to occur between a selected one of the electrodes and the reference electrode. Bipolar stimulation could likewise occur, e.g., between electrodes E1 and E2, or between E2 and E3, or between any other pair of electrodes.

In operation, using conventional stimulation, a stimulus current is applied to electrode E1, the stimulus location in the tissue 54 is essentially the location 56, adjacent the physical location of the electrode E1. Similarly, when a stimulus current is applied to electrode E2, the stimulus location in the tissue 54 is essentially centered at location 58, adjacent the physical location of the electrode E2. Likewise, when a stimulus current is applied to electrode E3, the stimulus location in the tissue 54 is essentially centered at location 60, adjacent the physical location of the electrode E3. It is thus seen that the resolution, or precision, with which a stimulus may be applied to the tissue is only as good as the spacing of the electrodes on the electrode array. That is, each stimulus location in the tissue 54 is separated by approximately the same distance "D" as separates the electrodes.

One strategy for escaping this limitation is to increase the number of electrodes and thereby decrease the inter-electrode spacing. However, such a strategy can only be carried to a limited extent, because at some point, believed to be around 16 to 22 electrodes, increasing the number of electrodes does not always improve spatial precision in stimulating the nerves on the cochlea. The electrical field gradient around a single stimulating electrode has an inherent, spatial imprecision. There is a fixed, ceiling number of discrete electrodes for each type of electrode array, beyond which, little improvement in spatial resolution will be seen.

The present invention, in contrast, goes beyond the limitations imposed by fixed electrodes by employing a current navigator 140 (FIG. 5B). In particular, current steering can be achieved by employing weighted delivery of simultaneous currents to through electrodes. The present invention also includes other forms for directing the stimulation—that is, where perceived stimulation results from employing virtual electrodes. Virtual electrodes may be achieved through current steering by delivering weighted currents simultaneously through at least two electrode or, alternatively, by delivering alternating stimuli through at least two electrodes in a time-multiplexed manner.

The present invention uses a current navigator 140 to process the dominant FTS component information and concurrently deliver stimuli to precise locations (places) in the cochlea. One technique to achieve this precise delivery, even between electrodes is to use current steering, by delivering stimuli simultaneously in weighted fashion to at least two electrodes in the array ($E_1 \ldots E_m$). By changing the weights of the relative currents delivered to each of the active electrodes, the peak excitation may be delivered to a location on the cochlea which more accurately reflects the dominant FTS component within a frequency band. Alternatively, as another technique, in accordance with the present method of the invention, the current navigator can use time-multiplexed, non-simultaneous delivery of alternating stimuli to implement virtual electrodes in order to precisely direct stimulation to places on the cochlea. In contrast, with conventional cochlear stimulation, the frequency representation delivered to an electrode is necessarily a fixed, spacial frequency which is disadvantageously dependent on the pre-determined position of an electrode on the cochlea.

Figure 7B:
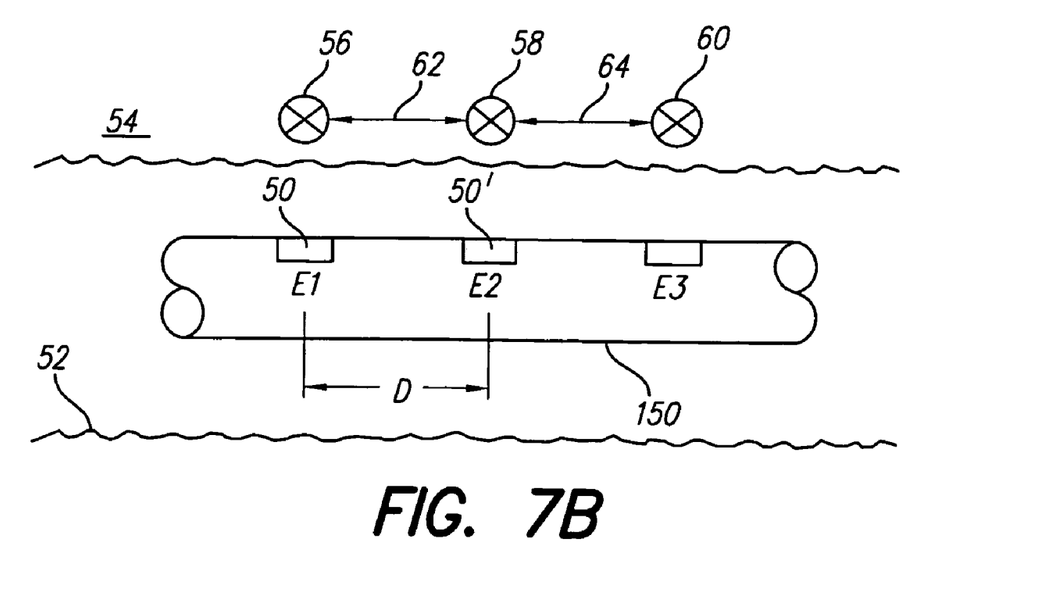
FIG. 7B illustrates the location of an applied stimulus within a duct of the cochlea, with the benefit of current steering.

With reference to FIG. 7B, a diagram is presented to illustrate the, location where a stimulus is applied when virtual electrodes are employed, e.g., current steering or, alternatively, time-multiplexed, non-simultaneous, alternating stimuli, in accordance with the present invention. The structure of the electrode array and spacing between electrodes E1, E2 and E3 is the same as in FIG. 3A. Thus, when a stimulus current is applied only to electrode E1, the stimulus location in the tissue 54 is the location 56, the same as was the case in FIG. 3A. Similarly, when a stimulus current is applied only to electrode E2, the stimulus location in the tissue 54 is the location 58. Likewise, when a stimulus current is applied only to electrode E3, a stimulus location in the tissue 54 is the location 60.

However, through the application of virtual electrodes, a stimulus current may be centered between two electrodes E1 and E2 (or even more than two electrodes), and the effective centered location of the stimulus, reflecting the position of the virtual electrode, can be anywhere along the line 62 between points 56 and 58. Alternatively, if the current is delivered between electrodes E2 and E3, the location in the tissue where the stimulus is centered may be anywhere along the line 64 between points 58 and 60.

Figure 8A:
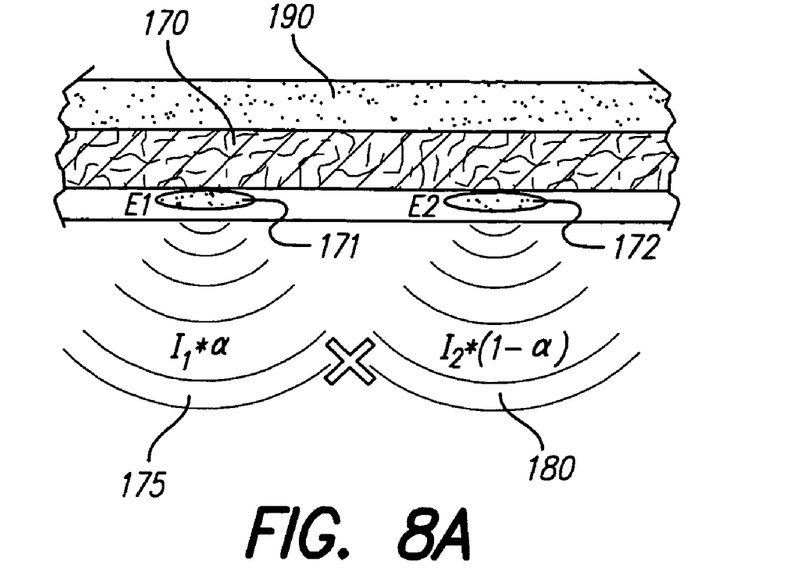
FIG. 8A provides an example of a virtual stimulation channel provided with a two electrode system for steering the current field.
Figure 8B:
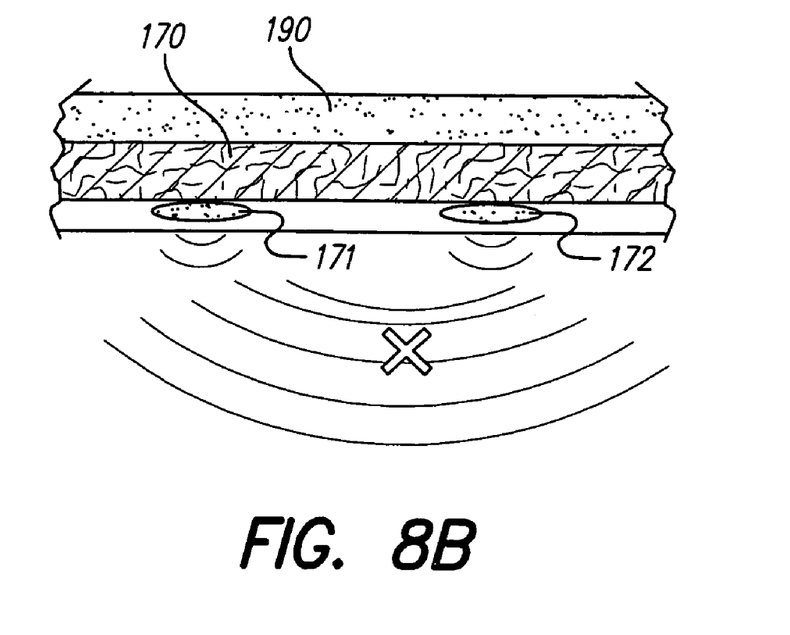
FIG. 8B provides another view of the same pair of electrodes in FIG. 8A, but with unequal current outputs between the two electrodes which skews the position of the highest intensity current field.

FIGS. 8A and 8B further illustrate, the implementation of virtual electrodes, through one technique, that is, the use of concurrent delivery of weighted stimuli from two electrodes. Current steering is achieved when two adjacent (cathodes) electrodes E1, 171, and E2, 172, are concurrently activated. A lead carrier 170 having the electrodes 171, 172 is placed into the one of the chambers of the cochlea, such as the scala tympani 190, and abutted against either a medial or the modiolar wall. At any given time, $I_1 * \alpha$ is applied to the first electrode 171, and $I_2 *(1-\alpha)$ is applied to a second, usually adjacent, electrode 172. Here, $I_1$ and $I_2$ represent current stimulation amplitudes and $\alpha$ is the fractional index (between 0 and 1) of the amplitude of $I_1$, relative to the amplitude of $I_2$. $I_1$ and $I_2$ are two pulse stimulus amplitudes such that, when presented on a first electrode 171 and a second electrode 172, respectively, have equal perceived loudness. The perceived loudness of a stimulation is determined by both its pulse amplitude and its rate of repetition (pulses per second).

The use of these two different values, $I_1$ and $I_2$, provides a calibration adjustment since placement of discrete electrodes is imprecise relative to target nerves and stimulation thresholds vary greatly between individual electrodes based on a number of factors. One of those factors is anatomical abnormalities in a patient in which some nerve bundles have died and, thus, particular areas of the cochlea may require more stimulation current to produce a given, perceived level of sound intensity.

By adjusting α, the peak excitation point can be spatially moved within the cochlea somewhere between the natural peak of the first electrode (α=0) and the natural peak of the second electrode (α=1). As shown in FIG. 8A, when $I_1$*α and $I_2$*(1−α) are approximately equal, the two fields 175 and 180 combine to provide a point of highest field strength somewhere between the two electrodes 171 and 172, depicted as point "X." As shown in FIG. 8B, the point X can be shifted by varying the relative values of $I_1$*α and $I_2$*(1−α).

The value of α can be computed (estimated) from the FTS analyzer/estimator 35 (FIG. 5B) using the formula: α=log{$F_{est}$(t)/$F_L$}/log {$F_H$/$F_L$}, where $F_{est}$(t) is the current peak frequency estimate, and $F_H$ and $F_L$ are the low and the high frequency limits of a single frequency band, respectively. The estimator processing software will set $I_1$ and $I_2$ to zero, if α is either larger than 1 or less than 0.

One embodiment of the method of the present invention for determining the values of $I_1$ and $I_2$ derives them from the envelope in a relevant channel. For example, if electrode pair (E1, E2) is used to represent channel 2, then $I_1$=(M1−T1)/IDR*log(envelope channel 2)+T1 (approximately), where M1 and T1 are the most comfortable and threshold levels of stimulus amplitudes, respectively, for electrode 1 and IDR is the input dynamic range. Similarly, $I_2$=(M2−T2)/IDR*log(envelope channel 2)+T2, where M2 and T2 are the most comfortable level and threshold level of stimulus amplitudes, respectively, for electrode 2. The "most comfortable level" is the stimulus level beyond which the stimulus becomes uncomfortable to the cochlear implant patient. The "threshold level" is the stimulus level which is just noticeable or just detectably perceived by the cochlear implant patient. The threshold level of stimulus can be incredibly small, amounting to a stimulus current that recruits just a few ganglion nerve fibers in the cochlea.

In an embodiment of the method of the present invention, if α is estimated to be larger than 1 or less than 0, then the stimulation during this frame is shifted to another stimulation channel. For example, if α equals 1.5, then, in accordance with the present invention, the navigator may direct stimulation to the next set of electrode pairs (E2, E3) using the relative weighting of 0.5. If this electrode pair is past the end of the available electrode pairs in the electrode array, then, to maintain stimulation continuity, only the last electrode in the array can be stimulated.

In another embodiment of the method of the present invention, intermediate pitch sensations may be produced, i.e., again using the concept of virtual electrodes, by stimulating two or more, usually closely-spaced, e.g., adjacent, electrodes in a rapidly alternating, time-multiplexed fashion. This technique may be employed when the pairs of electrodes are close together, such that the electric fields generated by the two electrodes overlap. Using this particular technique for implementing virtual electrodes, α can be estimated and obtained as described previously. The relative amplitudes of the electrode pair (E1, E2) may be set to values Ir($I_1$, α)*α and Ir($I_1$, α)*(1−α), where Ir($I_1$, α) is a function of I1, that would provide an absolute combined stimulus amplitude from electrode pair (E1, E2) which would result in an equivalent perceived loudness that would be produced by a stimulus current presented solely at one electrode, for instance, electrode E1 or electrode E2. In general, this function will be different for different electrode systems and must be estimated using standard loudness balancing techniques.

The advantage of this last technique is that it may implement virtual electrodes in cochlear system that does not support simultaneous stimulation at two electrodes. For example, such a system may not be able to provide independently controlled stimulus at two electrodes at the same time. However, a system may be able to rapidly present a sequence of stimuli in a non-concurrent, time-multiplexed fashion, e.g., stimulus presented in rapid sequence: E1, E2, E1, E2, . . . and so on, where the stimulus presented at the two electrodes may be different amplitudes. The net effect is to employ a virtual electrode somewhere between the two electrodes, E1 and E2.

Hence, through appropriate techniques of current delivery through two or more physical electrodes, to implement virtual electrodes, it is possible to thereby effectively direct the stimulus accurately to any location or place along the length of the electrode array and thus along the cochlear duct in which the array is implanted.

The output stage of the ICS 21 which connects with each electrode E1, E2, E3, . . . Em of the electrode array can be as described in U.S. Pat. No. 6,181,969, which patent is incorporated herein by reference. Such output stage can employ programmable N-DAC or P-DAC (where DAC stands for digital-to-analog converter) connected to each electrode so that a programmed current may be sourced to the electrode or sunk from the electrode. Such a configuration allows any electrode to be paired with any other electrode, and the amplitudes of the currents can be independently programmed and controlled to gradually shift the stimulating current that flows from one electrode through the tissue to another adjacent electrode or electrodes, thereby providing current steering. By "independently programmed" it is meant that delivery of each stimulus at each electrode may be current-controlled and separately programmed for pulsewidth, amplitude, and when the stimulus pulse is delivered (non-concurrently or concurrently). The N-DACs and/or P-DACs facilitates implementation of current steering or, alternatively, time-multiplexed, alternating delivery of stimuli.

A two electrode example for producing a virtual electrode has been described. It can be appreciated that three or more electrodes may be selected to interact together to produce a virtual electrode as well. In the two electrode example, both electrodes were cathodes and therefore operating in a monopolar electrode configuration. It is possible that one or more electrode may function as a return anode or anodes, thereby operating in a bipolar electrode configuration. A tripolar electrode arrangement is possible, wherein the middle electrode is an anode and the two outer electrodes are cathodes or vice-versa.

It is emphasized that the method of the invention, as represented in FIG. 5B, is not dependent on the use of particular implementations of a FTS estimator and the particular current navigator. Other embodiments of FTS analyzers/estimators or current navigators may be used with the present invention other than those specific embodiments which have been disclosed.

It is further emphasized that the present method can be used in conjunction with other stimulation concepts including use of (a) virtual electrodes and (b) M of N stimulation strategy. A M of N strategy is a stimulation strategy in which only M number of channels or electrodes are stimulated in one time interval of the N total available channels or electrodes. M is smaller than N, and both are whole numbers. Preferably, N is between 8 and 22 channels or electrodes. Virtual electrodes may be used in such a M of N stimulation system, provided that at least two electrodes are concurrently stimulated, e.g., M is at least 2.

While the invention herein disclosed has been described by means of specific embodiments and applications thereof, numerous modifications and variations could be made thereto by those skilled in the art without departing from the scope of the invention set forth in the claims.

What is claimed is:

1. A cochlear stimulation system for capturing and delivering fine time structure (FTS) in incoming sounds, the system comprising:
   an electrode array, having a plurality of electrodes for placing into a duct of a human cochlea;
   a plurality of stimulation channels connected to the electrode array, each stimulation channel connected to at least one electrode in the electrode array;
   an envelope extractor for extracting a slowly varying frequency envelope in the incoming sound;
   an FTS analyzer for estimating the FTS information within a frequency band; and
   a current navigator, which uses the identified dominant FTS component at each band of frequency and precisely directs, employing virtual electrodes, stimulation to each place of the cochlea that spatially corresponds to the identified dominant FTS component.

2. The system of claim 1, wherein the plurality of electrodes numbers between about 16 to 22.

3. The system of claim 1, wherein the FTS analyzer includes a software that employs Fast Fourier Transform to de-construct the incoming sound, within a pre-determined time interval, into dominant FTS components that are located in various frequency bands.

4. The system of claim 1, wherein the electrode array is inside the scala tympani.

5. The system of claim 1, wherein the FTS analyzer includes a software that extracts the number of zero-crossings in a pre-determined time interval to calculate the dominant FTS component in a frequency band.

6. The system of claim 5, wherein the pre-determined time interval is at least about 10 milliseconds.

7. The system of claim 1, wherein the FTS analyzer includes a software that extracts the averaged time duration between zero-crossing in a pre-determined time interval, in order to calculate the dominant FTS component in a frequency band.

8. The system of claim 7, wherein the pre-determined time interval is at least about 10 milliseconds.

9. The system of claim 1, wherein the current navigator linearly adds the carrier frequency and the dominant FTS component provided by the FTS analyzer, and wherein the current navigator precisely directs the stimulation to various electrodes.

10. The system of claim 1, wherein the cochlear stimulation system employs a M of N stimulation strategy.

11. A cochlear stimulation method for capturing and delivering FTS in incoming sounds, wherein the stimulation is provided by a plurality of electrodes in an electrode array connected to a multi-channel stimulator, the method comprising:
    analyzing the incoming sounds within a plurality of frequency bands;
    extracting the slowly varying frequency carrier component of the incoming sound in each frequency band with an envelope;
    estimating the dominant FTS component in each frequency band using an FTS analyzer;
    adding the dominant FTS component to the carrier component to provide a precise corresponding spatial location on the cochlea; and
    directing the stimulation current, using a current navigator, to the precise spatial place on the cochlea.

12. The method of claim 11, wherein the plurality of electrodes numbers between about 16 to 22.

13. The method of claim 11, wherein virtual electrodes are implemented either by simultaneous, weighted current steering or non-simultaneous, alternating, time-multiplexed presentation of stimuli in at least two electrode contacts.

14. The method of claim 11, further comprising:
    placing the electrode array inside the scala tympani.

15. The method of claim 11, wherein estimating the dominant FTS component is accomplished by using software in the FTS analyzer that extracts the number of zero-crossings in a pre-determined time interval.

16. The method of claim 14, wherein the pre-determined time interval is at least about 10 milliseconds.

17. The method of claim 11, wherein estimating the dominant FTS is accomplished by the FTS analyzer that de-constructs incoming sounds in a predetermined time interval, employing Fast Fourier Transformation.

18. The method of claim 17, wherein the pre-determined time interval is at least about 10 milliseconds.

19. The method of claim 11, wherein the step of adding the FTS information to the carrier is accomplished by linearly adding the two.

20. The method of claim 19, wherein the stimulation system employs a M of N stimulation strategy.

21. The method of claim 11, wherein the step of directing the stimulation current is accomplished by using virtual electrodes.

22. The method of claim 11, wherein estimating the dominant FTS is performed by taking the average of the time duration of intervals between zero-crossings.

* * * * *